United States Patent
Samain et al.

(10) Patent No.: US 6,497,864 B1
(45) Date of Patent: Dec. 24, 2002

(54) HAIRSTYLING COMPOSITION COMPRISING A POLYMER WITH PARTICULAR CHARACTERISTICS AND A NON-IONIC POLYMER

(75) Inventors: Henri Samain, Bièvres (FR); Christine Dupuis, Paris (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/600,976

(22) PCT Filed: Nov. 18, 1999

(86) PCT No.: PCT/FR99/02830

§ 371 (c)(1),
(2), (4) Date: Sep. 25, 2000

(87) PCT Pub. No.: WO00/30953

PCT Pub. Date: Jun. 2, 2000

(30) Foreign Application Priority Data

Nov. 26, 1998 (FR) ............................................. 98 14907

(51) Int. Cl.⁷ .............................. A61K 7/06; A61K 7/11
(52) U.S. Cl. ................... 424/70.1; 424/400; 424/70.11; 424/70.12; 424/70.16; 424/47
(58) Field of Search ............................. 424/70.1, 70.11, 424/70.12, 70.16, 47

(56) References Cited

U.S. PATENT DOCUMENTS 6,153,179 A * 11/2000 Blankenburg et al.

FOREIGN PATENT DOCUMENTS

| DE | 43 16 242 | 11/1994 |
| EP | 0 265 228 | 4/1988 |
| EP | 0 605 951 | 7/1994 |
| FR | 2 750 047 | 12/1997 |
| JP | 07-145023 | * 6/1995 |
| WO | WO 97/15275 | 5/1997 |

OTHER PUBLICATIONS

Patent Abstracts of Japan, vol. 096, No. 007, Jul. 31, 1996 (JP 08 081349).
"Avalure™ Film Forming Polymers for Personal Care Applications", BFGoodrich, TDS–248, Apr. 5, 1999, pp. 1–5.
English language Derwent Abstract of DE 43 16 242. (1994).
English language Derwent Abstract of FR 2 750 047. (1997).

* cited by examiner

*Primary Examiner*—Thurman K. Page
*Assistant Examiner*—Rachel M Bennett
(74) *Attorney, Agent, or Firm*—Finnegan, Henderson, Farabow, Garrett & Dunner, L.L.P.

(57) ABSTRACT

The invention concerns a hairstyling composition, in a cosmetically acceptable medium: (1) at least a polymer (A) selected such that the film obtained by drying a mixture of said polymer (A) with ethanol or water, at room temperature and a relative moisture content of 50%, has a mechanical profile defined by at least (i) an ultimate elongation rate ($\epsilon_r$) not less than 300%; (ii) a creep at 300 seconds ($R_{300}$) not less than 45%; and (iii) when the creep at 300 seconds ranges between 45 and 60% the elongation is less than 1300%; (2) at least a non-ionic film forming polymer (B), different from polymer (A). The invention also concerns a hairstyling of hair-fixing method using said composition and its use for formulating hairstyling products such as lacquers, sprays or foams, for hairstyling or hair-fixing.

28 Claims, No Drawings

HAIRSTYLING COMPOSITION COMPRISING A POLYMER WITH PARTICULAR CHARACTERISTICS AND A NON-IONIC POLYMER

This application is a 371 of PCT/FR99/02830 filed Nov. 18, 1999.

A subject-matter of the invention is a styling composition comprising, in a cosmetically acceptable medium, at least one polymer (A) with specific characteristics and at least one film-forming and nonionic polymer (B). It is also targeted at a process for shaping or retaining the form of the hair using this composition and at its use in the formulation of styling products, such as lacquers, sprays or mousses, for the purpose of obtaining form retention or shaping of the hairstyle.

The most widespread hair products on the cosmetics market for fixing the hair are compositions to be sprayed as an aerosol or as a pump-action spray, such as lacquers, sprays or mousses, composed essentially of a solution, generally an alcoholic or aqueous/alcoholic solution, and of a water-soluble or alcohol-soluble film-forming polymer, as a mixture with various cosmetic adjuvants.

However, these hair formulations, such as mousses, gels and especially aerosol sprays and lacquers intended to retain the form of the hairstyle, still do not make it possible for the hairstyle to satisfactorily withstand the various natural movements of life, such as walking, head movements or gusts of wind.

The polymers used for the formulation of these hair products are anionic, amphoteric or non-ionic film-forming polymers which result in the formation of films having a more or less hard and brittle nature.

When the polymer is too brittle, the percentage of elongation at break measured on the film is low, that is to say generally of less than 2%, and the hold of the hairstyle over time is not assured.

To overcome this problem, these polymers have already been mixed with plasticizers, and more flexible and non-flaky coatings have already been obtained. However, these films are deformable and plastic, that is to say that, after deformation, they only recover their initial form to a very small extent. While the hold of the hairstyle is improved, it is still not satisfactory since the form of the hairstyle changes over time.

More satisfactory results in terms of hold have been obtained with compositions comprising a combination of film-forming polymers, such as, for example, a cellulose polymer and an acrylic polymer. However, these compositions are still not entirely satisfactory, in so far as the hair loses some of its natural cosmetic properties.

There is therefore a search for cosmetic compositions for form retention of and/or for fixing the hairstyle which provide the hair with good cosmetic properties, in particular good disentangling, softness and a pleasant appearance, in addition to fixing which lasts.

Surprisingly and unexpectedly, the Applicant Company has discovered that it is possible to overcome the technical problems mentioned above by using certain specific combinations of polymers.

A subject-matter of the invention is a styling composition comprising, in a cosmetically acceptable medium:
(1) at least one polymer (A) chosen so that a film obtained by drying a mixture of this polymer (A) with ethanol or water, at room temperature and at a relative humidity level of 50%, exhibits a mechanical profile defined by at least:
  (i) a degree of elongation at break ($\epsilon_b$) of greater than or equal to 300%;
  (ii) a recovery at 300 seconds ($R_{300}$) of greater than or equal to 45%; and
  (iii) when the recovery at 300 seconds is between 45 and 60%, then the elongation is less than 1300%;
(2) at least one nonionic film-forming polymer (B), other than the polymer (A), chosen from
  polyalkyloxazolines;
  vinyl acetate homopolymers;
  copolymers of vinyl acetate and of acrylic ester;
  copolymers of vinyl acetate and of ethylene;
  copolymers of vinyl acetate and of maleic ester;
  copolymers of polyethylene and of maleic anhydride;
  alkyl acrylate homopolymers and alkyl methacrylate homopolymers;
  acrylic ester copolymers, such as, for example, copolymers of alkyl acrylates and of alkyl methacrylates;
  copolymers of acrylonitrile and of a nonionic monomer chosen from butadiene and alkyl (meth)acrylates,
  copolymers of alkyl acrylate and of urethane,
  guar gums,
  polymers derived from hydroxystyrene,
  vinyllactam homo- or copolymers.

Another subject-matter of the present invention relates to a process for shaping or retaining the form of the hairstyle comprising the use of this composition.

Yet another subject-matter of the present invention relates to the use of this composition in the manufacture of hair cosmetic compositions for the purpose of obtaining form retention or shaping of the hairstyle.

The polymers (A) particularly targeted by the present invention are those distributed by Goodrich under the name Avalure AC 315® and V29®.

Within the meaning of the present invention, the term "film obtained by drying at room temperature (22±2° C.) and at a relative humidity level of 50%±5%" is understood to mean the film obtained under these conditions starting from a mixture comprising 6% of active material (a.m.) of polymer A with ethanol or water, the amount of mixture being adjusted in order to obtain, in a Teflon matrix, a film with a thickness of 500±50 μm. The drying is continued until the weight of the film no longer changes, which represents approximately 12 days. The polymers A which are soluble or partially soluble in ethanol are tested in ethanol. The other polymers are tested in water, in the dissolved or dispersed form.

Within the meaning of the present invention, the degree of elongation at break and the degree of recovery are evaluated by means of the tests described below.

In order to carry out the tensile tests, the film is cut into rectangular test specimens with a length of 80 mm and a width of 15 mm.

The tests are carried out on a device, sold under the name Lloyd or sold under the name Zwick, under the same temperature and humidity conditions as for the drying, that is to say a temperature of 22±2° C. and a relative humidity level of 50±5%.

The test specimens are drawn at the rate of 20 mm/min and the distance between the jaws is 50±1 mm.

The following procedure is used to determine the instantaneous recovery ($R_i$):
  the test specimen is drawn by 150% ($\epsilon_{max}$), that is to say 1.5 times its initial length ($l_0$)
  the stress is released at a return rate equal to the tensile rate, i.e. 20 mm/min, and the elongation of the test specimen is measured as a percentage after returning to zero load ($\epsilon_i$).

The instantaneous recovery as a % ($R_i$) is given by the formula below:

$$R_i=((\epsilon_{max}-\epsilon_i)/\epsilon_{max})\times 100$$

In order to determine the recovery at 300 seconds, the test specimen which has been subjected to the preceding operations is maintained at zero stress for an additional 300 seconds and its degree of elongation is measured as a percentage ($\epsilon_{300}$)

The recovery as a % at 300 seconds ($R_{300}$) is given by the formula below:

$$R_{300}=((\epsilon_{max}-\epsilon_{300})/\epsilon_{max})\times 100$$

The nonionic film-forming polymers (B) which can be used according to the present invention are preferably chosen from:

vinylpyrrolidone or vinylcaprolactam homopolymers;

copolymers of vinylpyrrolidone and of vinyl acetate;

polyalkyloxazolines, such as the polyethyloxazolines provided by the company Dow Chemical under the names Peox 50,000, Peox 200,000 and Peox 500,000;

vinyl acetate homopolymers, such as the product provided under the name of Appretan EM by the company Hoechst or the product provided under the name of Rhodopas A 012 by the company Rhone-Poulenc;

copolymers of vinyl acetate and of acrylic ester, such as the product provided under the name of Rhodopas AD 310 from Rhône-Poulenc;

copolymers of vinyl acetate and of ethylene, such as the product provided under the name of Appretan TV by the company Hoechst;

copolymers of vinyl acetate and of maleic ester, for example dibutyl maleate, such as the product provided under the name Appretan MB Extra by the company Hoechst;

copolymers of polyethylene and of maleic anhydride;

alkyl acrylate homopolymers and alkyl methacrylate homopolymers, such as the product provided under the name Micropearl RQ 750 by the company Matsumoto or the product provided under the name Luhydran A 848 S by the company BASF;

acrylic ester copolymers, such as, for example, copolymers of alkyl acrylates and of alkyl methacrylates, such as the products provided by the company Röhm & Haas under the names Primal AC-261 K and Eudragit NE 30 D, by the company BASF under the names Acronal 601 or Luhydran LR 8833 or 8845, or by the company Hoechst under the names Appretan N 9213 or N 9212;

copolymers of acrylonitrile and of a nonionic monomer chosen, for example, from butadiene and alkyl (meth) acrylates; mention may be made of the products provided under the names Nipol LX 531 B by the company Nippon Zeon or those provided under the name CJ 0601 B by the company Röhm & Haas;

polyurethanes, such as the products provided under the names Acrysol RM 1020 or Acrysol RM 2020 by the company Röhm & Haas or the products Uraflex XP 401 UZ or Uraflex XP 402 UZ by the company DSM Resins;

copolymers of alkyl acrylate and of urethane, such as the product 8538-33 by the company National Starch;

polyamides, such as the product Estapor LO 11 provided by the company Rhône-Poulenc;

chemically modified or unmodified nonionic guar gums.

The unmodified nonionic guar gums are, for example, the products sold under the name Vidogum GH 175 by the company Unipectine and under the name Jaguar by the company Meyhall.

The modified nonionic guar gums which can be used according to the invention are preferably modified by $C_1$–$C_6$ hydroxyalkyl groups. Mention may be made, by way of example, of the hydroxymethyl, hydroxyethyl, hydroxypropyl and hydroxybutyl groups.

These guar gums are well known in the state of the art and can be prepared, for example, by reacting corresponding alkene oxides, such as, for example, propylene oxides, with guar gum, so as to obtain a guar gum modified by hydroxypropyl groups.

Such nonionic guar gums optionally modified by hydroxyalkyl groups are sold, for example, under the tradenames Jaguar HP8, Jaguar HP60, Jaguar HP120, Jaguar DC293 and Jaguar HP105 by the company Meyhall or under the name Galactasol 4H4FD2 by the company Aqualon.

The alkyl radicals of the nonionic polymers have from 1 to 6 carbon atoms, unless otherwise mentioned.

According to the invention, use may also be made of nonionic film-forming polymers derived from hydroxystyrene and in particular those capable of being obtained by the copolymerization of:

(i) at least one hydroxystyrene monomer, one of its precursors or one of its salts, the phenyl group of this monomer comprising at least one hydroxyl unit and optionally being substituted by one or more radicals chosen from the group consisting of $C_1$ to $C_{12}$ alkyl, $C_1$ to $C_{12}$ alkoxyalkyl, halogen, $SO_3H$, ($C_2$ to $C_{12}$) acylamino, carboxyl and $C_1$ to $C_{12}$ carboxyalkyl radicals, and (ii) at least one other monomer which is copolymerizable with the said hydroxystyrene monomer, one of its precursors or one of its salts, this other monomer being chosen from the group consisting of acrylic or methacrylic monomers or their derivatives, in particular linear, cyclic or branched $C_1$ to $C_{10}$ alkyl acrylates or methacrylates, such as methyl, ethyl, propyl, butyl, isobutyl, tert-butyl or 2-ethylhexyl acrylates or methacrylates, N-substituted or N,N'-substituted acrylamides or methacrylamides, and vinyl monomers, such as vinyl halides or vinyl esters, in particular vinyl benzoate, vinyl tert-benzoate or vinyl acetate.

The vinyl, acrylic or methacrylic monomers can comprise one or more siloxane groups. In this case, they are chosen in particular from the group consisting of:

monomers of formula $CH_2=C(CH_3)-C-O-(CH_2)_3-Si-O-Si(CH_3)_2-CH_3$, silicone macromonomers with a monofunctional vinyl, allyl, or ester ether or amide of acrylic or methacrylic acid ending, of formula $CH_2=C(R_1)-C-X-R_2-Si(CH_3)(R_4)-O-Si(CH_3)_2-R_3$, in which:

$R_1$ represents H or $CH_3$,

X represents O or NH, $R_2$ represents $(CH_2)_p$, p being an integer which can be zero, $R_3$ and $R_4$ independently represent $CH_3$ or an aliphatic, cycloaliphatic or aromatic $C_1$ to $C_{12}$ group; the vinyl, allyl, or ester ether or amide of acrylic or methacrylic acid monomer comprising one or more halogenated groups, in particular chlorinated and/or fluorinated groups, and/or comprising a group which absorbs in the UVA and/or UVB regions, in particular benzylidenecamphor or benzotriazole groups, which are substituted or unsubstituted.

The polymers of the hydroxystyrene type can also be obtained by a homopolymerization reaction which can advantageously be carried out from acetoxystyrene, in order to obtain poly-p-acetoxystyrene, and be followed by hydrolysis. It can also be carried out in acid medium from 4-hydroxyphenylmethylcarbinol.

According to this embodiment of the invention, the polymer is advantageously a homopolymer belonging to the family of the poly-p-hydroxystyrene and preferably poly-4-hydroxystyrene is chosen.

Within the meaning of the present invention, the term "precursor of a hydroxystyrene monomer" is understood to mean any phenolic derivative capable of resulting in hydroxystyrene via a decomposition reaction in acid medium, in particular by dehydration in acid medium. By way of example, the precursor can be acetoxystyrene or 4-hydroxyphenylmethylcarbinol and the decomposition reaction can, in this case, be represented diagrammatically in the following way:

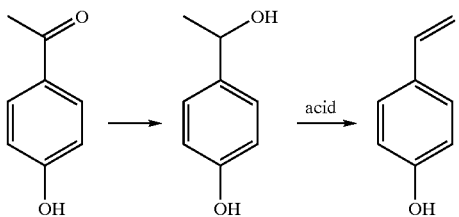

PHS-E is a homopolymer corresponding to the formula:

(PHS-E)

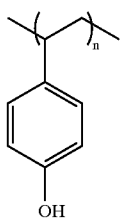

PHS-E is obtained from acetoxystyrene by means of radical polymerization, followed by hydrolysis. Its molecular mass is between 8000 and 100,000 g/mol. PHS-E is a linear polymer.

PHS-PG is a polymer corresponding to the formula:

(PHS-PG)

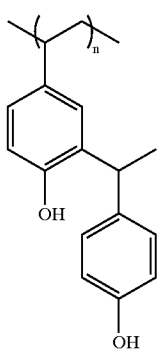

PHS-PG is obtained by catalysed polymerization in acid medium from 4-hydroxyphenylmethylcarbinol. Its molecular mass is between 4000 and 7000 g/mol.

PHS-N is a polymer corresponding to the formula:

(PHS-N)

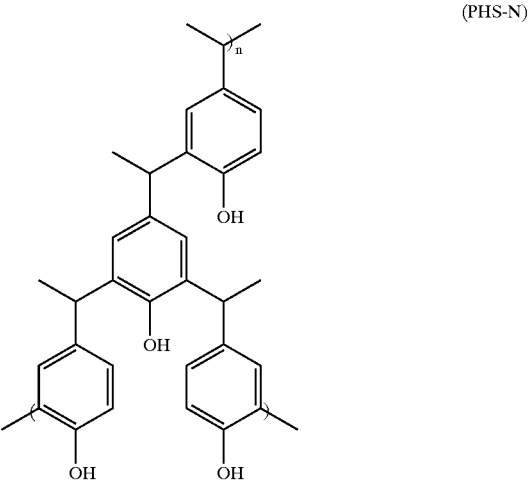

PHS-N is a polymer obtained by catalysed polymerization in acid medium of 4-hydroxyphenylmetylcarbinol. Its molecular mass is between 4000 and 7000 g/mol.

PHS-PG-L is a polymer exhibiting the same empirical formula as PHS-E. However, the process for producing it is different since the polymerization is carried out from hydroxystyrene monomers.

In the compositions in accordance with the invention, the film-forming polymer or polymers (A) are preferably present at concentrations of between 0.05 and 20% by weight, more preferably of between 0.1 and 15% by weight and more preferably between 0.25 and 10% by weight with respect to the total weight of the composition.

In the compositions in accordance with the invention, the film-forming polymer or polymers (B) are preferably present at concentrations of between 0.05 and 20% by weight, more preferably of between 0.1 and 15% by weight and more preferably between 0.25 and 10% by weight with respect to the total weight of the composition.

The concentrations of polymers (A) and (B) are advantageously chosen so that the ratio of the concentration of polymer (A) to the concentration of polymer CUB) is between 4000 and 0.002.

The cosmetically acceptable medium is preferably composed of water or one or more cosmetically acceptable solvents, such as alcohols or water/solvent(s) mixtures, these solvents preferably being $C_1$–$C_4$ alcohols.

Mention may be made, among these alcohols, of ethanol or isopropanol. Ethanol is particularly preferred.

The composition of the invention can also comprise at least one additive chosen from thickeners, surfactants, fragrances, preservatives, sunscreens, proteins, vitamins, inorganic or synthetic non-fixing polymers and any other additive conventionally used in cosmetic compositions intended to be applied to the hair.

Of course, a person skilled in the art will take care to choose the optional compound or compounds to be added to the composition according to the invention so that the advantageous properties intrinsically attached to the composition in accordance with the invention are not, or not substantially, detrimentally affected by the envisaged addition.

These compositions can be packaged in various forms, in particular in pump-action sprays or in aerosol containers, in order to ensure application of the composition in vaporized form or in mousse form. Such packaging forms are indicated, for example, when it is desired to obtain a spray, a lacquer or a mousse for fixing or treating the hair. The compositions in accordance with the invention can also be provided in the form of creams, of gels, of emulsions, of lotions or of waxes.

When the composition according to the invention is packaged in aerosol form for the purpose of obtaining a lacquer or a mousse, it comprises at least one propellant which can be chosen from volatile hydrocarbons, such as n-butane, propane, isobutane, pentane, a chlorinated and/or fluorinated hydrocarbon and their mixtures. Use may also be made, as propellant, of carbon dioxide gas, nitrous oxide, dimethyl ether (DME), nitrogen or compressed air. Use may also be made of mixtures of propellants. Dimethyl ether is preferably used.

The propellant is advantageously present at a concentration of between 5 and 90% by weight with respect to the total weight of the composition in the aerosol device and more particularly at a concentration of between 10 and 60%.

The compositions in accordance with the invention can be applied to dry or wet hair.

The invention will be more fully illustrated with the help of the following nonlimiting example.

All the percentages are relative percentages by weight with respect to the total weight of the composition and a.m. means active material.

EXAMPLE

A styling composition in accordance with the present invention, comprising Avalure AC315 as polymer (A) and polyvinylcaprolactam as polymer (B), and a composition in accordance with the prior art, comprising Avalure AC315 as polymer (A) and ethyl cellulose as polymer (B), are prepared. The formulations prepared are summarized in Table 1 below.

TABLE 1

|  | Composition 1 (prior art) | Composition 2 (invention) |
|---|---|---|
| Avalure AC315 | 1.5% | 2.65% |
| Ethyl cellulose | 0.2% | — |
| Polyvinylcaprolactam | — | 0.35% |
| Ethanol | q.s. 100 | q.s. 100 |

The two compositions, packaged as aerosols (composition 65%, DME 35%), are applied to locks of eurochestnut hair with a length of 18 cm and a weight of 20 grams.

The softness and the ease of disentangling of the hair after application of these compositions to the hair are evaluated by means of a sensory test with a panel of 5 people. The grades attributed range from 0 (poor performance) to 50 (excellent performance). The disentangling evaluated is the ease with which the comb can be run through after a first disentangling intended to break the polymer/individual hair structures.

The results obtained are summarized in Table 2 below.

TABLE 2

|  | Composition 1 (prior art) | Composition 2 (invention) |
|---|---|---|
| Softness | 10 | 20 |
| Disentangling | 20 | 25 |

It results from this that the compositions according to the invention provide better results in terms of softness and of disentangling than the compositions in accordance with the prior art.

What is claimed is:

1. A composition comprising:
   (1) at least one polymer (A) chosen such that a film obtained by drying a mixture of said at least one polymer (A) and at least one solvent chosen from ethanol and water, at room temperature and at a relative humidity level ranging from 45% to 55%, exhibits a mechanical profile defined by at least:
      (i) a degree of elongation at break ($\epsilon_b$) of greater than or equal to 300%; and
      (ii) a degree of recovery at 300 seconds ($R_{300}$) of greater than or equal to 45%;
      with the proviso that when said degree of recovery at 300 seconds ranges from 45% to 60%, said degree of elongation is less than 1300%; and
   (2) at least one nonionic film-forming polymer (B), different from said at least one polymer (A), chosen from polyalkyloxazolines, vinyl acetate homopolymers, copolymers of vinyl acetate and of acrylic ester, copolymers of vinyl acetate and of ethylene, copolymers of vinyl acetate and of maleic ester, copolymers of polyethylene and of maleic anhydride, alkyl acrylate homopolymers, alkyl methacrylate homopolymers, acrylic ester copolymers, copolymers of acrylonitrile and of at least one nonionic monomer chosen from butadiene and alkyl (meth)acrylates, copolymers of alkyl acrylate and of urethane, guar gums, polymers derived from hydroxystyrene, vinyllactam homopolymers, and vinyllactam copolymers.

2. A composition according to claim 1, wherein said vinyllactam homopolymers are chosen from vinylcaprolactam homopolymers.

3. A composition according to claim 1, wherein said polymers derived from hydroxystyrene are chosen from linear polymers obtainable from hydroxystyrene and branched polymers obtainable from hydroxystyrene, and further wherein said polymers derived from hydroxystyrene are obtainable from homopolymerization or copolymerization of at least one monomer chosen from hydroxystyrene monomers, precursors of hydroxystyrene monomers, and salts of hydroxystyrene monomers, wherein the phenyl group of said at least one monomer comprises at least one hydroxyl radical; and wherein the phenyl group of said at least one monomer may optionally be substituted by at least one group chosen from $C_1$ to $C_{12}$ alkyl groups, $C_1$ to $C_{12}$ alkoxyalkyl groups, halogens, $SO_3H$ groups, ($C_2$ to $C_{12}$) acylamino groups, carboxyl groups, and $C_1$ to $C_{12}$ carboxyalkyl groups.

4. A composition according to claim 3, wherein said polymers derived from hydroxystyrene are chosen from polymers obtainable from copolymerization of:
   (i) at least one monomer chosen from hydroxystyrene monomers, precursors of hydroxystyrene monomers, and salts of hydroxystyrene monomers, wherein the phenyl group of said at least one monomer comprises at least one hydroxyl radical; and wherein the phenyl group of said at least one monomer may optionally be substituted by at least one group chosen from $C_1$ to $C_{12}$ alkyl groups, $C_1$ to $C_{12}$ alkoxyalkyl groups, halogens, $SO_3H$ groups, ($C_2$ to $C_{12}$) acylamino groups, carboxyl groups and $C_1$ to $C_{12}$ carboxyalkyl groups; and (ii) at least one additional monomer, different from said at least one monomer (i), wherein said at least one additional monomer is copolymerizable with said at least one monomer (i), and wherein said at least one additional monomer is chosen from linear $C_1$ to $C_{10}$ alkyl acrylate monomers, cyclic $C_1$ to $C_{10}$ alkyl acrylate monomers, branched $C_1$ to $C_{10}$ alkyl acrylate monomers, linear $C_1$ to $C_{10}$ alkyl methacrylate monomers, cyclic $C_1$ to $C_{10}$ alkyl methacrylate monomers, branched $C_1$ to $C_{10}$ alkyl methacrylate monomers, N-substituted acrylamide monomers, N,N'-substituted acrylamide monomers, N-substituted methacrylamide monomers, N,N'-substituted methacrylamide monomers, and vinyl monomers.

5. A composition according to claim 4, wherein said vinyl monomers are chosen from vinyl halides and vinyl esters.

6. A composition according to claim 5, wherein said vinyl esters are chosen from vinyl benzoate, vinyl tert-benzoate, and vinyl acetate.

7. A composition according to claim 4, wherein said at least one additional monomer further comprises at least one siloxane group.

8. A composition according to claim 7, wherein said at least one additional monomer is chosen from:

(a) monomers of formula:

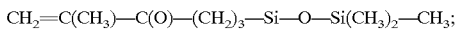

$CH_2=C(CH_3)-C(O)-(CH_2)_3-Si-O-Si(CH_3)_2-CH_3$;

and (b) silicone macromonomers comprising at least one group (i) chosen from vinyl groups, allyl groups, ester ethers of acrylic acid, ester ethers of methacrylic acid, amides of acrylic acid, and amides of methacrylic acid, wherein said silicone macromonomers have a formula:

$CH_2=C(R_1)-(CX)-R_2-Si(CH_3)(R_4)-O-Si(CH_3)_2-R_3$, wherein:

$R_1$ is chosen from H and $CH_3$;

CX is chosen from C=O and $CH_2NH$;

$R_2$ is chosen from $(CH_2)_p$, wherein p is an integer;

$R_3$ and $R_4$, which are identical or different, are each chosen from aliphatic $C_1$ to $C_{12}$ groups, cycloaliphatic $C_1$ to $C_{12}$ groups, and aromatic $C_1$ to $C_{12}$ groups, and wherein said at least one group (i) comprises at least one moiety chosen from halogenated groups and groups which absorb light in at least one region chosen from the UVA region and the UVB region.

9. A composition according to claim 8, wherein said at least one moiety is chosen from benzylidenecamphor groups, optionally substituted, and benzotriazole groups, optionally substituted.

10. A composition according to claim 1, wherein said guar gums are chosen from modified nonionic guar gums and unmodified nonionic guar gums.

11. A composition according to claim 10, wherein said modified nonionic guar gums are modified with $C_1-C_6$ hydroxyalkyl groups.

12. A composition according to claim 1, wherein said acrylic ester copolymers are chosen from copolymers of alkyl acrylate monomers and of alkyl methacrylate monomers.

13. A composition according to claim 1, further comprising at least one cosmetically acceptable medium.

14. A composition according to claim 13, wherein said at least one cosmetically acceptable medium is chosen from water and cosmetically acceptable solvents.

15. A composition according to claim 14, wherein said cosmetically acceptable solvents are chosen from alcohols.

16. A composition according to claim 15, wherein said alcohols are chosen from $C_1-C_4$ alcohols.

17. A composition according to claim 16, wherein said $C_1-C_4$ alcohols are chosen from ethanol and isopropanol.

18. A composition according to claim 1, wherein said at least one polymer (A) is present in an amount ranging from 0.05% to 20% by weight relative to the total weight of the composition.

19. A composition according to claim 18, wherein said at least one polymer (A) is present in an amount ranging from 0.25% to 10% by weight with respect to the total weight of said composition.

20. A composition according to claim 1, wherein said at least one nonionic film-forming polymer (B) is present in an amount ranging from 0.05% to 20% by weight with respect to the total weight of said composition.

21. A composition according to claim 20, wherein said at least one nonionic film-forming polymer (B) is present in an amount ranging from 0.25% to 10% by weight with respect to the total weight of said composition.

22. A composition according to claim 1, wherein the ratio of said at least one polymer (A) to said at least one nonionic film-forming polymer (B) ranges from 0.002 to 4000.

23. A composition according to claim 1, further comprising at least one cosmetic additive.

24. A composition according to claim 23, wherein said at least one cosmetic additive is chosen from fatty substances, thickening agents, softeners, antifoaming agents, moisturizing agents, antiperspirants, basifying agents, dyes, pigments, surfactants, fragrances, preservatives, sunscreens, proteins, vitamins, inorganic non-fixing polymers and synthetic non-fixing polymers.

25. A composition according to claim 1, wherein said composition is in the form of a cream, a gel, an emulsion, a lotion, a mousse, a hairspray, or a wax.

26. An aerosol device comprising at least one propellant and at least one composition comprising:

(1) at least one polymer (A) chosen such that a film obtained by drying a mixture of said at least one polymer (A) and at least one solvent chosen from ethanol and water, at room temperature and at a relative humidity level ranging from 45% to 55%, exhibits a mechanical profile defined by at least:

(i) a degree of elongation at break ($\epsilon_b$) of greater than or equal to 300%; and (ii) a degree of recovery at 300 seconds ($R_{300}$) of greater than or equal to 45%;

with the proviso that when said degree of recovery at 300 seconds ranges from 45% to 60%, said degree of elongation is less than 1300%; and (2) at least one nonionic film-forming polymer (B), different from said at least one polymer (A), chosen from polyalkyloxazolines, vinyl acetate homopolymers, copolymers of vinyl acetate and of acrylic ester, copolymers of vinyl acetate and of ethylene, copolymers of vinyl acetate and of maleic ester, copolymers of polyethylene and of maleic anhydride, alkyl acrylate homopolymers, alkyl methacrylate homopolymers, acrylic ester copolymers, copolymers of acrylonitrile and of at least one nonionic monomer chosen from butadiene and alkyl (meth)acrylates, copolymers of alkyl acrylate and of urethane, guar gums, polymers derived from hydroxystyrene, vinyllactam homopolymers, and vinyllactam copolymers.

27. A process for holding or shaping the hair, comprising applying to said hair an effective amount of a composition comprising:

(1) at least one polymer (A) chosen such that a film obtained by drying a mixture of said at least one polymer (A) and at least one solvent chosen from ethanol and water, at room temperature and at a relative humidity level ranging from 45% to 55%, exhibits a mechanical profile defined by at least:
  (i) a degree of elongation at break ($\epsilon_b$) of greater than or equal to 300%; and
  (ii) a degree of recovery at 300 seconds ($R_{300}$) of greater than or equal to 45%;
  with the proviso that when said degree of recovery at 300 seconds ranges from 45% to 60%, said degree of elongation is less than 1300%; and
(2) at least one nonionic film-forming polymer (B), different from said at least one polymer (A), chosen from polyalkyloxazolines, vinyl acetate homopolymers, copolymers of vinyl acetate and of acrylic ester, copolymers of vinyl acetate and of ethylene, copolymers of vinyl acetate and of maleic ester, copolymers of polyethylene and of maleic anhydride, alkyl acrylate homopolymers, alkyl methacrylate homopolymers, acrylic ester copolymers, copolymers of acrylonitrile and of at least one nonionic monomer chosen from butadiene and alkyl (meth)acrylates, copolymers of alkyl acrylate and of urethane, guar gums, polymers derived from hydroxystyrene, vinyllactam homopolymers, and vinyllactam copolymers.

28. A process for improving the holding or shaping power of a composition comprising including in said composition:
(1) at least one polymer (A) chosen such that a film obtained by drying a mixture of said at least one polymer (A) and at least one solvent chosen from ethanol and water, at room temperature and at a relative humidity level ranging from 45% to 55%, exhibits a mechanical profile defined by at least:
  (i) a degree of elongation at break ($\epsilon_b$) of greater than or equal to 300%; and
  (ii) a degree of recovery at 300 seconds ($R_{300}$) of greater than or equal to 45%;
  with the proviso that when said degree of recovery at 300 seconds ranges from 45% to 60%, said degree of elongation is less than 1300%; and
(2) at least one nonionic film-forming polymer (B), different from said at least one polymer (A), chosen from polyalkyloxazolines, vinyl acetate homopolymers, copolymers of vinyl acetate and of acrylic ester, copolymers of vinyl acetate and of ethylene, copolymers of vinyl acetate and of maleic ester, copolymers of polyethylene and of maleic anhydride, alkyl acrylate homopolymers, alkyl methacrylate homopolymers, acrylic ester copolymers, copolymers of acrylonitrile and of at least one nonionic monomer chosen from butadiene and alkyl (meth)acrylates, copolymers of alkyl acrylate and of urethane, guar gums, polymers derived from hydroxystyrene, vinyllactam homopolymers, and vinyllactam copolymers.

* * * * *

UNITED STATES PATENT AND TRADEMARK OFFICE
CERTIFICATE OF CORRECTION

PATENT NO.   : 6,497,864 B1
DATED        : December 24, 2002
INVENTOR(S)  : Henri Samain et al.

It is certified that error appears in the above-identified patent and that said Letters Patent is hereby corrected as shown below:

<u>Title page,</u>
Item [57], ABSTRACT,
Line 1, after "composition", insert -- comprising --.

Signed and Sealed this

Twenty-seventh Day of May, 2003

JAMES E. ROGAN
*Director of the United States Patent and Trademark Office*